(12) United States Patent
Dai

(10) Patent No.: US 9,539,087 B2
(45) Date of Patent: Jan. 10, 2017

(54) INTRAVITREOUS SELF ADAPTIVE STENT

(75) Inventor: Rongping Dai, Beijing (CN)

(73) Assignee: EMPIRE TECHNOLOGY DEVELOPMENT LLC, Wilmington, DE (US)

( * ) Notice: Subject to any disclaimer, the term of this patent is extended or adjusted under 35 U.S.C. 154(b) by 892 days.

(21) Appl. No.: 13/123,440

(22) PCT Filed: Apr. 28, 2010

(86) PCT No.: PCT/CN2010/072281
§ 371 (c)(1),
(2), (4) Date: Apr. 8, 2011

(87) PCT Pub. No.: WO2011/134146
PCT Pub. Date: Nov. 3, 2011

(65) Prior Publication Data
US 2012/0035738 A1    Feb. 9, 2012

(51) Int. Cl.
| | | |
|---|---|---|
| A61F 2/14 | (2006.01) |
| A61F 2/844 | (2013.01) |
| A61F 2/92 | (2013.01) |
| A61F 2/848 | (2013.01) |
| A61F 2/82 | (2013.01) |
| A61L 31/02 | (2006.01) |
| A61L 31/06 | (2006.01) |
| A61L 31/14 | (2006.01) |
| A61L 31/16 | (2006.01) |

(52) U.S. Cl.
CPC ............. *A61F 2/14* (2013.01); *A61F 2/844* (2013.01); *A61F 2/92* (2013.01); *A61F 2/82* (2013.01); *A61F 2/848* (2013.01); *A61L 31/022* (2013.01); *A61L 31/06* (2013.01); *A61L 31/14* (2013.01); *A61L 31/16* (2013.01)

(58) Field of Classification Search
CPC ............ A61F 2/14; A61F 2/844; A61F 2/848; A61F 2/92
USPC ......... 623/4.1, 6.63–6.64, 23.64, 23.67–23.7
See application file for complete search history.

(56) References Cited

U.S. PATENT DOCUMENTS

| | | | |
|---|---|---|---|
| 3,174,851 A | 3/1965 | Buehler et al. | |
| 6,666,841 B2 | 12/2003 | Gharib et al. | |
| 2004/0193262 A1* | 9/2004 | Shadduck | 604/8 |
| 2007/0073016 A1 | 3/2007 | Alvarado et al. | |
| 2007/0179426 A1* | 8/2007 | Selden | 604/8 |
| 2009/0062906 A1 | 3/2009 | Ozawa et al. | |

FOREIGN PATENT DOCUMENTS

| | | |
|---|---|---|
| CN | 101049270 | 10/2007 |
| EP | 1 570 870 | 9/2005 |

OTHER PUBLICATIONS

D'Amico, D.J., "Primary Retinal Detachment," The New England Journal of Medicine, Nov. 27, 2008, vol. 359, pp. 2346-2354.
Frank, R.N., "Diabetic Retinopathy," Engl J Med, Jan. 1, 2004, vol. 350, pp. 48-58.

(Continued)

*Primary Examiner* — Howie Matthews
(74) *Attorney, Agent, or Firm* — Foley & Lardner LLP

(57) ABSTRACT

Disclosed herein are devices, methods and kits for a stent for treating an eye, comprising a flexible material, wherein the stent is self adaptive to a dimension of a vitreous cavity in the eye.

19 Claims, 7 Drawing Sheets

(56) References Cited

OTHER PUBLICATIONS

Gariano R.F. and Kim, C.H. "Evaluation and Management of Suspected Retinal Detachment," American Family Physician, Apr. 1, 2004, vol. 69, No. 7, pp. 1691-1698.
International Search Report and Written Opinion for PCT/CN2010/072281 mailed Feb. 10, 2011.
Gupta, V. et al., "Nitinol thin film three-dimensional devices—fabrication and applications," Proceedings of the International Conference on Shape Memory and Superelastic Technology, 2004, 8 pages.
Yasukawa, T. et al., "Intraocular sustained drug delivery using implantable polymeric devices," Adv. Drug Deliv. Rev., 2005, vol. 57, No. 14, pp. 2033-2046.
Database WPI, Week 200816, Thomson Scientific, AN 2008-C08866, XP-002717143, for CN 101049270A dated Oct. 10, 2007, 1 page.
Extended European Search Report received for EP Appln. 10850479.6 dated Dec. 10, 2013.
Refojo, M., et al., "Optical Properties of Gels Designed for Vitreous Implantation," Jun. 2, 2973, Invest. Opthalmol. Vis. Sci., vol. 12, No. 6, pp. 465-467.

* cited by examiner

INTRAVITREOUS SELF ADAPTIVE STENT

CROSS-REFERENCE TO RELATED APPLICATION

The present application is a U.S. national stage application under 35 U.S.C. §371 of International Application No. PCT/CN2010/072281, filed on Apr. 28, 2010, the entire content of which is incorporated herein by reference in its entirety.

BACKGROUND

Proliferative vitreoretinopathy (PVR) is a catastrophic complication of a retinal detachment (RD) and can cause profound visual loss. PVR is a scar tissue formation within the eye and is typically treated by surgeries.

Treatment for PVR includes, but is not limited to, e.g., pars plana vitrectomy, membrane peeling where small instruments are used to peel the membranes from the surface of the retina, and scleral buckling. These techniques are combined with fluids placed in the eye to flatten the retina and reattach it to the outer wall of the retina followed by laser photocoagulation to connect the retina permanently. Typically, the fluids used are perfluoron (PFO) or perfluoro-n-octane which are heavier-than-water fluid and push the retina into its normal position. When injected, PFO settles to the back of the eye and pushes the subretinal fluid to the front. Alternatively, a gas bubble is placed in the eye to hold the retina in place while it is healing, or as another alternative, silicone oil is used to hold the retina in its position. Disadvantages of the gas bubble include, but are not limited to, that the patient must restrict the movement of their head for two to three weeks following surgery before they can go back to normal activities. Disadvantages of the silicone oil bubble include, but are not limited to, that the patient requires removal of the oil in several months following the procedure. Additional disadvantages of both the gas bubble and the silicone bubble include that these techniques may lead to secondary glaucoma and may not be effective to inferior retina.

More than 500,000 vitrectomy surgeries are performed annually in the world. About 80% of surgeries are performed with temporary tamponade, such as gas, silicone oil or heavy silicone oil of which about 10% surgeries are not successful. There is a need for efficient and simple treatment of eye diseases related to retinal detachment.

SUMMARY

In one aspect of the present technology, there is provided a stent for treating an eye, comprising a flexible material, wherein the stent is self adaptive to a dimension of a vitreous cavity in the eye.

In some embodiments, the flexible material comprises silicon, styrene, polypropylene, polyurethane, poly(caprolactone-β-ethylene oxide), poly(L-lactide-co-glycolide), and polytetrafluoroethylene.

In some embodiments, the flexible material comprises an aliphatic ester C1-C50 of acrylic acid or a methacrylic acid ester of polyethyleneoxide. In some embodiments, the aliphatic ester C1-C50 of acrylic acid is an aliphatic ester C1-C50 of methacrylic acid. In some embodiments, the aliphatic ester C1-C50 of acrylic acid includes, but is not limited to, butyl acrylate, polyarcylic acid, poly(methyl methacrylimide), pentafluoropropylacrylate, polyethylene glycol methacrylate, polyethyleneglycol monomethylether methacrylate, methylmethacrylate, poly(methyl methacrylate), isobornyl methacrylate, isobutyl methacrylate, perfluoroacetylmethacrylate, tertiary butylmethacrylate, phenylethylmethacrylate, hydroxyethyl methacrylate, glycerol methacrylate, and heptadecylfluorodecyl-methacrylate. In some embodiments, the methacrylic acid ester of polyethyleneoxide is polyethyleneglycol dimethacrylate, polyethyleneglycol methacrylate or polyethyleneglycol acrylate.

In some embodiments, the flexible material comprises a shape memory substance. In some embodiments, the shape memory substance is a titanium-nickel (Ti—Ni) based shape memory alloy. In some embodiments, the Ti—Ni based shape memory alloy is Ti at about 43.5-52 weight percent and Ni at about 48-56.5 weight percent. In some embodiments, the Ti—Ni based shape memory alloy is Ti at about 44.4 weight percent and Ni at about 55.6 weight percent. In some embodiments, the Ti—Ni based shape memory alloy is Ti—Ni—X alloy where X is at least one selected from Fe, V, Cr, Co, and Nb. In some embodiments, the Ti—Ni based shape memory alloy is Ti at about 43.5-51 weight percent, Ni at about 40-56.5 weight percent, and X at about 0-9 weight percent. In some embodiments, the Ti—Ni based shape memory alloy is Ti at about 43.5-51 weight percent, Ni at about 40-56.5 weight percent, and Nb at about 0-9 weigh percent.

In some embodiments, the Ti—Ni based shape memory alloy is in a form of a wire, mesh, or plate. In some embodiments, the Ti—Ni based shape memory alloy is of an annular shape at a body temperature and a folded shape at room temperature.

In some embodiments, the flexible material is a biodegradable material or a non-biodegradable material. In some embodiments, the biodegradable material is poly (caprolactone-β-ethylene oxide) or poly(L-lactide-co-glycolide). In some embodiments, the non-biodegradable material is a Ti—Ni based shape memory alloy, poly(acrylic acid), and poly(methyl methacrylimide).

In some embodiments, the flexible material is biologically compatible.

In some embodiments, the stent is of an annular shape at a body temperature. In some embodiments, the annular shape has a diameter which approximates a diameter of the vitreous cavity of the eye.

In some embodiments, the annular shape has a diameter in a range of about 8 mm to about 30 mm. In some embodiments, the annular shape has a narrower region with the diameter in a range of about 8 mm to about 26 mm and a wider region with the diameter in a range of about 12 mm to about 30 mm.

In some embodiments, the annular shape has a diameter in a range of about 14 mm to about 24 mm. In some embodiments, the annular shape has a narrower region with the diameter in a range of about 14 mm to about 20 mm and a wider region with the diameter in a range of about 16 mm to about 24 mm. In some embodiments, the annular shape has a narrower region with the diameter of about 20 mm and a wider region with the diameter of about 22 mm.

In some embodiments, the annular shape has a height in a range of about 2 to about 8 mm. In some embodiments, the annular shape has a height in a range of about 3 to about 6 mm. In some embodiments, the annular shape has a height of about 5 mm.

In some embodiments, the stent is configured for implantation in a vitreous cavity of the eye.

In some embodiments, the stent is self adaptive to the dimension of the vitreous cavity in the eye by a self adaptive zone. In some embodiments, the self adaptive zone is a closed region or an open region in the stent. In some embodiments, the self adaptive zone has a width in a range of about 1-8 mm.

In some embodiments, the stent of the present technology further comprises an optional means for fixing the stent in the eye. In some embodiments, the stent of the present technology further comprises an optional one or more projections for fixing the stent in the eye. In some embodiments, the one or more projections comprise one or more regions in the stent which are sutured inside the eye.

In some embodiments, the stent of the present technology further comprises a therapeutic agent. In some embodiments, the therapeutic agent is coated on to the stent. In some embodiments, the therapeutic agent is present inside the flexible material. In some embodiments, the therapeutic agent includes, but is not limited to, anti-proliferative drugs, neuron protective drugs, antibiotics, anti-inflammatory, glaucoma drug, anti-viral, and anti-allergy agent.

In some embodiments, there is provided a stent for treating an eye comprising a titanium-nickel (Ti—Ni) based shape memory alloy, which stent is self adaptive to a dimension of a vitreous cavity in the eye, wherein the Ti—Ni based shape memory alloy is of an annular shape in a parent phase region and a folded shape in a martensite region, wherein the annular shape has a narrower region with the diameter of about 20 mm and a wider region with the diameter of about 22 mm, and wherein the annular shape has a height of about 5 mm.

In one aspect of the present technology, there is provided a method of treating an ocular disease in a subject, comprising implanting a stent in an eye of the subject wherein the stent comprises a flexible material, and wherein the stent is self adaptive to a dimension of a vitreous cavity in the eye.

In some embodiments, the stent is implanted into a vitreous cavity of the eye by injection. In some embodiments, the stent is injected into the eye using a catheter. In some embodiments, the stent is manually injected into the eye.

In some embodiments of the method aspect, the flexible material comprises a titanium-nickel (Ti—Ni) based shape memory alloy. In some embodiments, the Ti—Ni based shape memory alloy of the stent is of a folded shape before implantation. In some embodiments, the Ti—Ni based shape memory alloy of the stent restores an annular shape at a body temperature after implantation in the eye.

In some embodiments, the stent supports a detached retina or proliferative membrane near an equator of the eye.

In some embodiments, the method aspect of the present technology further comprises suturing the stent to sclera at pars plana of ciliary body in the eye.

In some embodiments, the ocular disease is vitreoretinopathy.

In some embodiments of the method aspect, the stent is self adaptive to the dimension of the vitreous cavity in the eye of the subject by a self adaptive zone.

In some embodiments of the method aspect, the subject is human.

In another aspect of the present technology, there is provided a method of treating vitreoretinopathy in a subject, comprising implanting a stent in an eye of the subject wherein the stent comprises a flexible material, and wherein the stent is self adaptive to a dimension of a vitreous cavity in the eye, thereby treating the vitreoretinopathy in the subject.

In another aspect of the present technology, there is provided a kit comprising a stent for treating an eye, wherein the stent comprises a flexible material, and wherein the stent is self adaptive to a dimension of a vitreous cavity in the eye.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

FIG. 4A depicts an illustrative embodiment of an annular shape of the stent where the self adaptive zone is a closed region; FIG. 4B depicts a frontal view of the annular shaped stent; FIG. 4C depicts a frontal view of the stent that is being folded in the middle; and FIG. 4D depicts a cross sectional view of the stent that is being folded in the middle.

FIG. 5A depicts an illustrative embodiment of an annular shape of the stent where the self adaptive zone is an open region; FIG. 5B depicts a frontal view of the stent that is being folded in the middle; FIG. 5C depicts a cross sectional view of the stent that is being rolled or twined inwards; and FIG. 5D depicts a cross sectional view of the stent where each end of the open region of the stent has been folded inwards.

DETAILED DESCRIPTION

Figure 1:
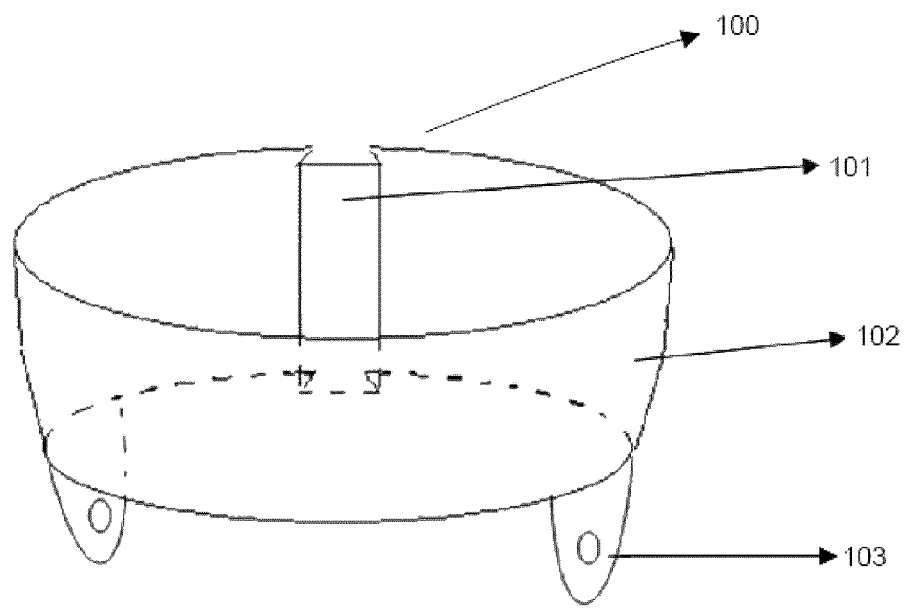
FIG. 1 depicts an illustrative embodiment of a stent of the present technology.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

The present technology is described herein using several definitions, as set forth throughout the specification. As used herein, unless otherwise stated, the singular forms "a," "an," and "the" include plural reference.

The term "comprising" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude trace contaminants from the isolation and purification method and pharmaceutically acceptable carriers, such as phosphate buffered saline, preservatives and the like. "Consisting of" shall mean excluding more than trace elements of other ingredients and substantial method steps for administering the compositions of this technology or process steps to produce a composition or achieve an intended result. Embodiments defined by each of these transition terms are within the scope of this technology.

One aspect includes a stent for treating an eye, that is composed of a flexible material and that is self adaptive to a dimension of a vitreous cavity in the eye. In some embodiments of the present technology, the stent is configured for implantation in the vitreous cavity of the eye. The dimension of the vitreous cavity may vary depending on the species, gender or age of the subject. For example, the vitreous cavity of a child or an infant is smaller than the vitreous cavity of an adult subject. The vitreous cavity in the present technology is intended to include eye of any mammalian species including from infant, to juvenile, and to adult.

The self adaptive nature of the flexible material may be dependent on the design and/or the material used for the stent. For example, when the flexible material is a shape memory alloy, as described herein, then the stent is self adaptive to the dimension of the vitreous cavity in the eye after the alloy deforms at the body temperature. Alternatively, when the flexible material is a polymeric material as described herein, such as polyacrylic acid, then the stent is self adaptive to the dimension of the vitreous cavity in the eye by virtue of the flexibility of the material. In some embodiments, the design of the stent can include a closed region and/or an open region (as described below) that adapts to the size and/or shape of the vitreous cavity in the eye. The self adaptive characteristic of the flexible material may result in an approximation of the shape and/or size of the stent to the dimension of the vitreous cavity in the eye. The flexible materials are well known in the art and various examples of such flexible material are provided herein. The flexible material of the stent also aids in the folding of the stent prior to implantation. After implantation of the stent, the flexible material restores the shape that fits the vitreous cavity of the eye.

Figure 2:
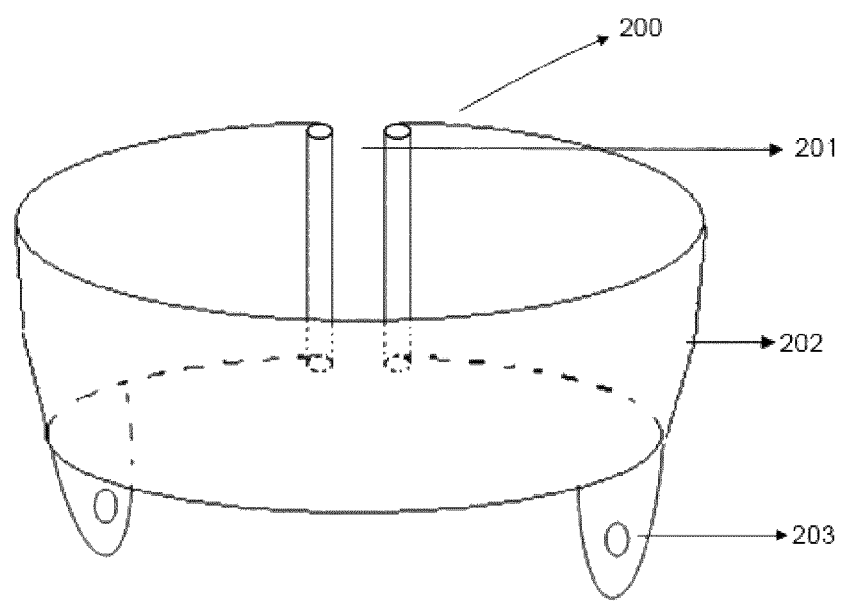
FIG. 2 depicts another illustrative embodiment of a stent of the present technology.

Illustrative embodiments of the stent of the present technology are depicted in FIGS. 1 and 2. It is to be understood that the stents depicted in FIGS. 1 and 2 are for illustration purposes only and various alterations in shape, size, and/or features of the stent are well within the scope of the present technology. The stent in both FIGS. 1 and 2 is of an annular shape and is made of Titanium-Nickel (Ti—Ni) alloy or polymer thereof which Ti—Ni alloy or polymer thereof, is as described below. FIGS. 1 and 2 depict an annular shape of the stent 100 and 200, respectively, which is the shape of the stent before and/or after its implantation in the eye. The stent 100 or 200 may optionally be folded during its storage and/or before the implantation and/or in preparation for the implantation of the stent in the eye.

In some embodiments, the stent is self adaptive to the dimension of the vitreous cavity in the eye by a self adaptive zone. The self adaptive zone may be a closed region or an open region in the stent. The illustrative stent 100 in FIG. 1 comprises a self adaptive zone 101 which is shown as a closed region in the stent in this embodiment. This closed region is folded inwards in such a way that it allows the stent to increase or decrease its diameter based on the size of the vitreous cavity. In another embodiment, the illustrative stent in FIG. 2 comprises a self adaptive zone 201 which is shown as an open region in the stent. This open region allows the stent to increase or decrease its diameter based on the size of the vitreous cavity. In some embodiments, a combination of these self adaptive approaches and other approaches of the sort may be configured in the stent. The self adaptive zone 101 or 201 in the stent adjusts or modulates a shape and/or size of the stent with respect to (and optionally in response to) the size and/or shape of the vitreous cavity of the subject. The adjustment or the modulation of the shape and/or size of the stent leads to the placement of the stent into the vitreous cavity of the eye in such a way that the detached retina is restored in its place.

The stent in FIG. 1 or 2 is in a form of a wire 102 or 202, respectively, that is wound around to take the annular shape. Alternatively, the stent can be in a form of a mesh or a net; alternatively, the stent can be in a form of a plate; or further alternatively, the stent can be in a form of a plate with holes in it. It is to be understood that stent can be in any form that fits into the vitreous cavity of the eye and allows circulation of oxygen and the fluid in the eye through the stent.

In some embodiments of the present technology, the stent optionally has one or more means for fixing the stent in the eye. In some embodiments of the present technology, the stent optionally has one or more locations and/or projections configured for fixing the stent in the eye. The means or one or more locations and/or projections for fixing the stent in the eye are illustrated in both FIGS. 1 and 2 as legs 103 and 203, respectively. In some embodiments, the stent may have one or multiple legs or projections, or just locations with an opening provided to allow for attachment to the inside of the eye. In some embodiments, the stent may have other shapes of the attachment point such as, but not limited to, spherical, rectangular, square, etc., so long as there is a desire for means for fixing the stent in the eye. In some embodiments, no such means for fixing the stent or the projections are needed in the stent.

The one or more means for fixing the stent or the projections, such as 103 or 203 in FIGS. 1 and 2 respectively, comprise one or more regions in the stent which are configured for attachment to inside of the eye (e.g. through sutures). An illustrative embodiment of the one or more such regions are depicted in FIGS. 1 and 2 as holes in the leg 103 or 203. In an alternative embodiment, the one or more means for fixing the stent are configured to be attached to the retina of the eye using a biocompatible adhesive (e.g. a biocompatible glue). Such biocompatible adhesives are known in the art and include without limitation polyacrylate adhesives. In some embodiments, the one or more means for fixing the stent or the locations or the projections, such as 103 or 203 in FIGS. 1 and 2 respectively, comprise a hook or a hole in it such that the stent is sutured or glued or attached through the hook or the hole to the eye. In some embodiments, the one or more means for fixing the stent are absent in the stent and the stent attaches to the retina through, for example, but not limited to, sheer elastic force or through the uneven surface of the stent. Any number of variations of the means for fixing the stent or such locations or projections are known to a skilled artisan and they are all within the scope of the present technology.

In an alternative embodiment, an intraocular lens may be attached to the stent of the present technology which is then attached to the retina of the eye. Such stent with an attached intraocular lens can be used to treat eyes which either need an intraocular lens or need a replacement of the existing intraocular lens in addition to vitreoretinopathy. In one illustrative embodiment, such stent would not only provide the intraocular lens to the subject but would also attach to the retina of the eye of the subject.

Examples of the flexible material for all the embodiments of the stent, are as provided below. In some embodiments, the flexible material of the stent includes, but is not limited to, silicon, styrene, polypropylene, polyurethane, and polytetrafluoroethylene.

In some embodiments of the stent as described herein, the flexible material of the stent is an aliphatic ester C1-C50 of acrylic acid or a methacrylic acid ester of polyethyleneoxide. In some embodiments, the aliphatic ester C1-C50 of acrylic acid is an aliphatic ester C1-C50 of methacrylic acid.

In some embodiments of the stent as described herein, the flexible material of the stent is an aliphatic ester C1-C50 of acrylic acid which includes, but is not limited to, butyl acrylate, polyarcylic acid, pentafluoropropylacrylate, polyethylene glycol methacrylate, polyethyleneglycol monomethylether methacrylate, methylmethacrylate, poly(methyl methacrylate), isobornyl methacrylate, isobutyl methacrylate, perfluoroacetylmethacrylate, tertiary butylmethacrylate, phenylethylmethacrylate, hydroxyethyl methacrylate, glycerol methacrylate, and heptadecylfluorodecyl-methacrylate.

In some embodiments of the stent as described herein, the flexible material of the stent is poly(methyl methacrylate), polyarcylic acid, or hydroxyethyl methacrylate.

In some embodiments of the stent as described herein, the flexible material of the stent is the methacrylic acid ester of polyethyleneoxide which includes, but is not limited to, polyethyleneglycol dimethacrylate, polyethyleneglycol methacrylate or polyethyleneglycol acrylate.

In some embodiments of the stent as described herein, the flexible material of the stent is a shape memory substance. In some embodiments, the shape memory substance is a titanium-nickel (Ti—Ni) based shape memory alloy or polymer thereof. The shape memory alloy is an alloy that remembers its original, cold, forged shape (martensite phase) and which returns to that shape after being deformed by applying heat (austenitic or parent phase). The shape memory alloy, such as a Ti—Ni alloy, exhibits a remarkable shape memory effect in association with martensitic reverse transformation and exhibits spontaneous shape recovery and spring characteristics (superelasticity) in a parent phase region after the reverse transformation from a martensite region (see U.S. Pat. No. 3,174,851 and US Publication No. 20090062906, incorporated herein by reference in their entirety).

The Ti—Ni shape memory alloy of the present technology is characterized in that, at a temperature above a reverse transformation finish temperature (Af point) at which reverse transformation of the alloy starting from a reverse transformation start temperature (As point) is finished, the alloy that has been deformed under an external load is recovered into an original shape simultaneously when the external load is released. Herein, the As point means a shape recovery start temperature while the Af point means a shape recovery finish temperature (shape recovery temperature). The alloy has the Af point not lower than a living body temperature (around 37° C. or as appropriate for the animal or mammal or life stage).

In one embodiment, a stent is formed into an annular shape in its cold state where the annular shape has a size that would substantially fit the size of the vitreous cavity of the eye of the subject. The stent is optionally folded prior to implantation into the eye of the subject. When the stent is implanted into the vitreous cavity of the eye, the stent recovers spontaneously into its original diameter at body temperature and comes into contact with the retina in the vitreous cavity of the eye. Thus, the stent restores the detached retina in the eye.

In some embodiments of the present technology, the Ti—Ni based shape memory alloy comprises Ti at about 43.5-52 weight percent and corresponding Ni at about 48-56.5 weight percent. In some embodiments of the present technology, the Ti—Ni based shape memory alloy comprises Ti at about 43.5-52 weight percent; or alternatively 43.5-45 weight percent; or alternatively 43.5-46 weight percent; or alternatively 43.5-48 weight percent; or alternatively 43.5-50 weight percent; or alternatively 45-52 weight percent; or alternatively 45-50 weight percent; or alternatively 45-48 weight percent; or alternatively 47-52 weight percent; or alternatively 47-49 weight percent; or alternatively 48-52 weight percent; or alternatively 48-50 weight percent; or alternatively 49-52 weight percent; or alternatively 50-52 weight percent, with a corresponding weight percent of Ni.

In some embodiments of the present technology, the Ti—Ni based shape memory alloy comprising above recited Ti comprises Ni at about 48-56.5 weight percent; or alternatively 48-50 weight percent; or alternatively 48-52 weight percent; or alternatively 48-54 weight percent; or alternatively 48-56 weight percent; or alternatively 50-56.5 weight percent; or alternatively 50-52 weight percent; or alternatively 50-54 weight percent; or alternatively 50-56 weight percent; or alternatively 52-56.5 weight percent; or alternatively 52-54 weight percent; or alternatively 54-56.5 weight percent, with a corresponding weight percent of Ti.

In some embodiments, the Ti—Ni based shape memory alloy comprises Ti at about 44.4% and Ni at about 55.6%. In some embodiments, the Ti—Ni based shape memory alloy comprises Ti at about 45% and Ni at about 55%. In some embodiments, the Ti—Ni based shape memory alloy comprises Ti at about 44% and Ni at about 56%. In some embodiments, the Ti—Ni based shape memory alloy comprises Ti at about 43.5% and Ni at about 56.5%. In some embodiments, the Ti—Ni based shape memory alloy comprises Ti at about 46% and Ni at about 54%.

In some embodiments of the present technology, the Ti—Ni based shape memory alloy in the shape memory substance of the stent comprises Ti—Ni—X alloy where X is at least one selected from iron (Fe), vanadium (V), chromium (Cr), cobalt (Co), and niobium (Nb). In some embodiments, the Ti—Ni based shape memory alloy comprises Ti, Ni, and Fe. In some embodiments, the Ti—Ni based shape memory alloy comprises Ti, Ni, and V. In some embodiments, the Ti—Ni based shape memory alloy comprises Ti, Ni, and Cr. In some embodiments, the Ti—Ni based shape memory alloy comprises Ti, Ni, and Co. In some embodiments, the Ti—Ni based shape memory alloy comprises Ti, Ni, and Nb.

In some embodiments of the present technology, the Ti—Ni based shape memory alloy in the shape memory substance of the stent comprises Ti—Ni—X—Y alloy where X is at least one selected from iron (Fe), vanadium (V), chromium (Cr), cobalt (Co), or niobium (Nb) and Y is at least one selected from copper (Cu) or zirconium (Zr). In some embodiments of the present technology, the Ti—Ni based shape memory alloy in the shape memory substance of the stent comprises Ti—Ni—X—Y—Z alloy where X is at least one selected from iron (Fe), vanadium (V), chromium (Cr), cobalt (Co), or niobium (Nb); Y is copper (Cu); and Z is zirconium (Zr).

In some embodiments, the Ti—Ni based shape memory alloy comprises Ti at about 43.5-51 weight percent, Ni at about 40-56.5 weight percent, and X at about 0-9 at weigh percent. In some embodiments, the Ti—Ni based shape memory alloy comprises Ti at about 43.5-51 weight percent, Ni at about 40-56.5 weight percent, and Fe, V, Cr, Co, or Nb at about 0-9 weigh percent. In some embodiments, the Ti—Ni based shape memory alloy comprises Ti at about 43.5-51 weight percent; Ni at about 40-56.5 weight percent; Fe, V, Cr, Co, or Nb at about 0-5 weigh percent; and Cu and/or Zr at about 0-4 weight percent.

In some embodiments, the flexible material of the stent is a non-biodegradable material. The term "biodegradable" is intended to refer to a material that breaks down into smaller fragments by the natural environment. Such non-biodegradable stent may stay in the eye until it is surgically removed from the eye. Examples of such non-degradable materials include, but are not limited to, Ti—Ni shape memory alloy, poly(acrylic acid) and poly(methyl methacrylimide).

In some embodiments, the flexible material of the stent is a biodegradable material. Examples of such biodegradable materials include, but are not limited to, poly(caprolactone-β-ethylene oxide) or poly(L-lactide-co-glycolide). Such biodegradable materials suitable for the stent of the present technology are well known in the art and are well within the scope of the present technology. In some embodiments, the biodegradable material degrades in the eye with in the period of from about 1 week to about 5 years; or alternatively with in the period of from about 2 week to about 3 years; or alternatively with in the period of from about 2 week to about 2 years; or alternatively with in the period of from about 2 week to about 1 year; or alternatively with in the period of from about 2 week to few months.

In some embodiments, the flexible material of the stent of the present technology is biologically compatible. The term "biologically compatible" is intended to refer to a material that does not substantially react with the human body and does not cause any substantial allergic reaction. By "substantial," it is intended that the material does not cause a reaction that is beyond the tolerable limits of the subject or the reaction subsides after a few hours or days.

In some embodiments of the present technology, the flexible material of the stent is in a form of a wire, mesh, or plate. In some embodiments, the Ti—Ni based shape memory alloy is in a form of a wire, mesh, or plate.

In some embodiments of the present technology, the Ti—Ni based shape memory alloy is of an annular shape in a parent phase region and a folded shape in a martensite region. In some embodiments of the present technology, the stent is of an annular shape at a body temperature. In some embodiments of the present technology, the Ti—Ni based shape memory alloy is of an annular shape at a body temperature and a folded shape at room temperature.

In some embodiments of the present technology, the Ti—Ni based shape memory alloy restores an annular shape at a body temperature.

In some embodiments of the present technology, the annular shape of the stent has a diameter which approximates a diameter of the vitreous cavity of the eye.

In some embodiments of the present technology, the Ti—Ni based shape memory alloy of the stent is of a folded shape before implantation.

In some embodiments of the present technology, the Ti—Ni based shape memory alloy of the stent restores an annular shape at a body temperature after implantation in the eye.

Figure 3:
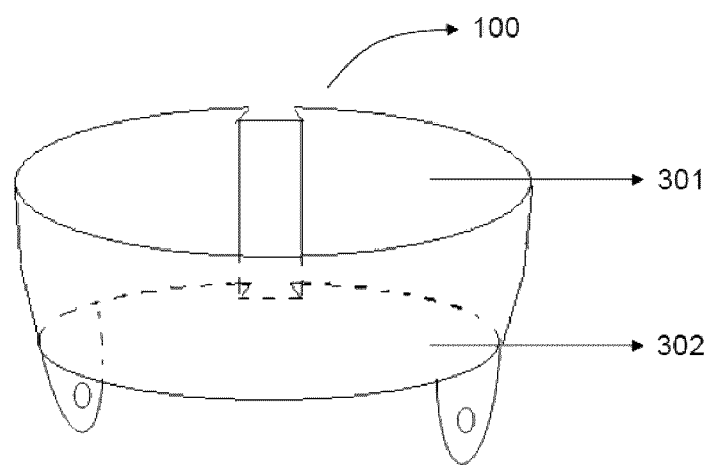
FIG. 3 depicts an illustrative embodiment of various regions in the stent of the present technology.
Figure 3:
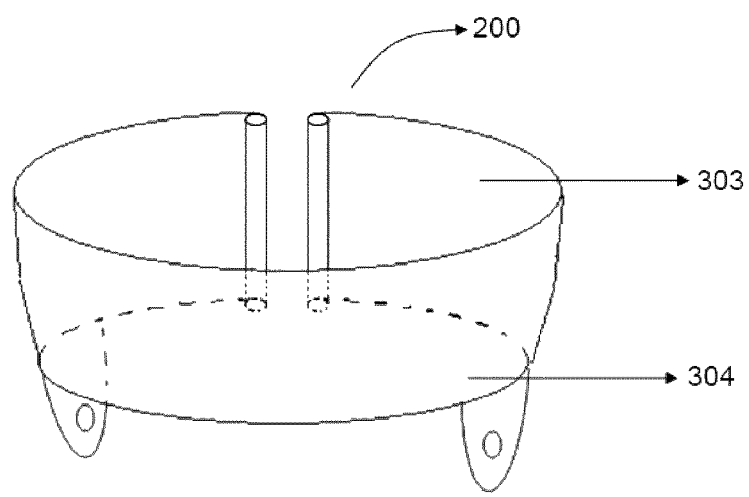

FIG. 3 depicts an illustrative embodiment of the stent of the present technology showing the stent 100 with a wider region 301 and a narrower region 302 or the stent 200 with a wider region 303 and a narrower region 304. The wider region 301 or 303 and the narrower region 302 or 304 in the stent are configured in such a way that the stent contours to adapt the shape of the vitreous cavity in the eye. It is to be understood that the stent of FIG. 3 is for illustration purposes only and that various deviations from the depicted contouring of the stent are well within the scope of the skilled artisan. For example, the wider region, such as 301 and 303 of the stent, may not be at one end of the stent. The wider region can be in the middle of the stent such that the stent is narrower at the two ends or the wider region can be at one third of the width of the stent such that the stent is narrower at the two ends. Alternatively, the stent may be alternately narrow and wide throughout the width of the stent in a form of a wave. The stent can be of any shape, dimension, and/or size so long as it is configured to support the retina of the eye of the desired subject. The dimension of the stent will vary depending on the size of the vitreous cavity in the eye of the subject.

Some illustrative dimensions of the stent of the present technology are as provided below. It is to be understood that the dimensions can apply to different embodiments of the stent as described herein.

In some embodiments of the present technology, the stent or the annular shape of the stent has a diameter in a range of about 8 mm to about 30 mm; or alternatively about 8 mm to 28 mm; or alternatively about 8 mm to 25 mm; or alternatively about 8 mm to 20 mm; or alternatively about 8 mm to 15 mm; or alternatively about 12 mm to 28 mm; or alternatively about 12 mm to 25 mm; or alternatively about 12 mm to 20 mm; or alternatively about 12 mm to 18 mm; or alternatively about 12 mm to 15 mm; or alternatively about 14 mm to 30 mm; or alternatively about 14 mm to 24 mm; or alternatively about 14 mm to 22 mm; or alternatively about 14 mm to 20 mm; or alternatively about 14 mm to 18 mm; or alternatively about 14 mm to 16 mm; or alternatively about 16 mm to 30 mm; or alternatively about 16 mm to 25 mm; or alternatively about 16 mm to 22 mm; or alternatively about 16 mm to 20 mm; or alternatively about 16 mm to 18 mm; or alternatively about 20 mm to 30 mm; or alternatively about 20 mm to 25 mm; or alternatively about 20 mm to 22 mm; or alternatively about 22 mm to 30 mm; or alternatively about 22 mm to 24 mm; or alternatively about 18 mm to 22 mm.

In some embodiments of the present technology, the stent has a diameter in a range of about 8 mm to about 30 mm. In some embodiments of the present technology, the stent has a diameter in a range of about 14 mm to about 24 mm. In some embodiments of the present technology, the annular shape of the stent has a diameter in a range of about 14 mm to about 24 mm.

In some embodiments of the present technology, the stent has a narrower region with the diameter in a range of about 8 mm to about 26 mm; or alternatively in a range of about 8 mm to about 20 mm; or alternatively in a range of about 8 mm to about 15 mm; or alternatively in a range of about 8 mm to about 10 mm; or alternatively in a range of about 10 mm to about 25 mm; or alternatively in a range of about 10 mm to about 20 mm; or alternatively in a range of about 10 mm to about 15 mm; or alternatively in a range of about 14 mm to about 16 mm; or alternatively about 14 mm to 18 mm; or alternatively about 14 mm to 20 mm.

In some embodiments of the present technology, the stent has a wider region with the diameter in a range of about 12 mm to about 30 mm; or alternatively in a range of about 12 mm to about 25 mm; or alternatively in a range of about 12 mm to about 20 mm; or alternatively in a range of about 16 mm to about 30 mm; or alternatively in a range of about 16 mm to about 24 mm; or alternatively about 16 mm to 20 mm; or alternatively in a range of about 20 mm to about 30 mm; or alternatively about 20 mm to 22 mm; or alternatively about 22 mm to 24 mm; or alternatively about 16 mm to 18 mm; or alternatively about 18 mm to 22 mm.

In some embodiments of the present technology, the stent or the annular shape of the stent has a narrower region with the diameter in a range of about 8 mm to about 26 mm and a wider region with the diameter in a range of about 12 mm to about 30 mm; or alternatively narrower region with the diameter in a range of about 10 mm to about 25 mm and a wider region with the diameter in a range of about 15 mm to about 30 mm; or alternatively narrower region with the diameter in a range of about 15 mm to about 20 mm and a wider region with the diameter in a range of about 20 mm to about 30 mm.

In some embodiments of the present technology, the stent or the annular shape of the stent has a narrower region with the diameter in a range of about 14 mm to about 20 mm and a wider region with the diameter in a range of about 16 mm to about 24 mm; or alternatively narrower region with the diameter in a range of about 16 mm to about 20 mm and a wider region with the diameter in a range of about 18 mm to about 24 mm; or alternatively narrower region with the diameter in a range of about 20 mm to about 22 mm and a wider region with the diameter in a range of about 18 mm to about 20 mm.

In some embodiments of the stent as described above, the stent has a narrower region with the diameter of about 20 mm and a wider region with the diameter of about 22 mm. In some embodiments of the stent as described above, the annular shape of the stent has a narrower region with the diameter of about 20 mm and a wider region with the diameter of about 22 mm.

In some embodiments of the stent as described above, the stent has a height in a range of about 2 mm to about 8 mm; or alternatively 3 mm to about 6 mm. In some embodiments of the stent as described above, the stent has a height of about 3 mm; or alternatively about 4 mm; or alternatively about 5 mm; or alternatively about 6 mm; or alternatively about 7 mm; or alternatively about 8 mm. In some embodiments of the stent as described above, the stent has a height of about 5 mm.

In some embodiments of the stent as described above, the annular shape of the stent has a height in a range of about 2 mm to about 8 mm; or alternatively 3 mm to about 6 mm. In some embodiments, the annular shape of the stent has a height of about 3 mm; or alternatively about 4 mm; or alternatively about 5 mm; or alternatively about 6 mm; or alternatively about 7 mm; or alternatively about 8 mm. In some embodiments of the stent as described above, the annular shape of the stent has a height of about 5 mm.

In some embodiments of the stent as described above, the self adaptive zone, as illustrated in FIGS. 1 and 2 as 101 and 201 respectively, has a width in a range of about 1 mm to about 8 mm. In some embodiments of the stent as described above, the self adaptive zone has a width of about 1 mm; or alternatively about 2 mm; or alternatively about 3 mm; or alternatively about 4 mm; or alternatively about 5 mm; or alternatively about 6 mm; or alternatively about 7 mm; or alternatively about 8 mm; or alternatively in a range of about 2-4 mm; or alternatively in a range of about 4-6 mm; or alternatively in a range of about 6-8 mm.

In some embodiments of the stent as described above, the stent further comprises a therapeutic agent. In some embodiments, the therapeutic agent is coated on to the stent. In some embodiments, the therapeutic agent is directly coated onto the stent. In some embodiments, the therapeutic agent is mixed in a polymeric matrix before being coated onto the stent. A coating, typically of a polymer, may hold and elute (release) the therapeutic agent into the eye by contact transfer. Examples of such polymers include, but are not limited to, poly-n-butyl methacrylate and polyethylene-vinyl acetate copolymer or poly(lactide-co-Σ-caprolactone) copolymer. The coating may be designed to biodegrade after or as the drug is eluted. Coatings may typically be spray coated or dip coated by dipping the stent into the polymer. There can be one to three or more layers in the coating e.g. a base layer for adhesion, a main layer for holding the agent, and optional top coat to slow down the release of the drug and extend its effect.

In some embodiments, the therapeutic agent is present inside the flexible material. The therapeutic agent may be embedded inside the flexible material or attached to the flexible material. In some embodiments, the therapeutic agent is configured for release into the eye. In some embodiments, the therapeutic agent is present in a sustained release device attached to the stent. Examples of such sustained release device include, but are not limited to, intraocular sustained-release ganciclovir implant. This implant is a polymeric device shaped in a form of a disc and is used for the treatment of cytomegalovirus (CMV) retinitis. It can be placed directly into an infected eye where the implant slowly releases ganciclovir, a drug used to treat CMV infection. See Yasukawa et al. "Intraocular sustained drug delivery using implantable polymeric devices" *Adv Drug Deliv Rev*. (2005) 13:57(14):2033-46. In some embodiments, the device or the implant is attached to the stent. In some embodiments, the device or the implant attached to the stent is in a shape including, but not limited to, sheet, disc, rod, plug, or a larger device.

The therapeutic agent can be any agent known in the art that can be administered to the eye. In some embodiments of the stent as described above, the therapeutic agent is selected from the group consisting of anti-proliferative agent, neuron protective agents, antibiotics, anti-inflammatory, glaucoma drug, anti-viral, and anti-allergy agents.

VEGF is responsible for the growth of new blood vessels. It promotes this growth by stimulating the endothelial cells, which form the walls of the vessels and transport nutrients and oxygen to the tissues. When the retinal pigment epithelial (RPE) cells begin to wither from lack of nutrition (a condition called "ischemia"), the VEGF goes into action to create new vessels. This process is called neovascularization, and it acts as a restorative function in other parts of the body. In the retina, however, the vessels do not form properly, and leaking results. This leakage causes scarring in the macula and eventual loss of central vision.

Anti-proliferative agents or anti-VEGF agents prevent the VEGF from binding with the receptors on the surface of the endothelial cells. Neovascularization is then blocked, preventing bleeding into the retina. Examples of anti-proliferative drugs include, but are not limited to, actinomycin, colchicine, cytosine arabinoside hydrochloride, 5-fluorodeoxyuridine, vinblastine sulfate, daunomycin, Macugen® (pegaptanib sodium), Lucentis® (ranibizumab), Tryptophanyl-tRNA synthetase (TrpRS), AdPEDF, VEGF-Trap-Eye, Avastin® (bevacizumab), Sirolimus® (rapamycin), and endostatin.

A neuronal death can be a result of episodes of anoxia and ischaemia in the retina and other eye diseases, such as anterior ischemic optic neuropathy, glaucoma etc. The neuronal death can be due to the accumulation of glutamate in the extracellular space. Glutamate is the primary excitatory neurotransmitter in the retina. However, excessive overactivation of glutamate receptors can lead to excitotoxic neuronal cell death. Glutamate excitoxicity can also cause neuronal mitochondrial membrane potential (MMP) loss, which is associated with changes in mitochondrial function leading to a neuronal dysfunction. Ginkgo biloba extract 761 (EGb761) is a standardized extract of the Ginkgo biloba. EGb761 is an example of a neuron protective agent that has a neuro-protective effect in many nervous system diseases, such as neurodegenerative diseases, anoxia and ischemia, and peripheral nerve damage. Another example of neuron protective agent is a nerve growth factor (NGF). The "nerve growth factor" or "NGF" refers to any biologically active form of NGF, such as, but not limited to, e.g., NGF β-subunit, either natural or recombinant, hybrid or modified forms of NGF that bind to their corresponding receptor and preserve the bioavailability of NGF, or NGF fragments or hybrids in which some amino acids have been eliminated or substituted, on condition that the resulting product maintains a sufficient capacity to bind to the specific receptor.

Antibiotics are generally used to treat, or sometimes to prevent a bacterial eye infection. Examples of antibiotics include, but are not limited to, vancomycin, cephalosporins, sulfacetamide, erythromycin, gentamicin, tobramycin, ciprofloxacin, ofloxacin, or combination thereof.

Anti-inflammatory agent can reduce inflammation, which in the eye is usually manifested by pain, redness, light sensitivity and blurred vision. Examples of anti-inflammatory agents include, but are not limited to, corticosteroids such as triamcinolone acetonide, prednisolone, fluorometholone, or dexamethasone; and non-steroids such as, diclofenac, ketorolac, or flurbiprofen, or combination thereof.

Glaucoma medications attempt to reduce the eye's intraocular pressure, the fluid pressure inside the eye, to prevent damage to the optic nerve resulting in loss of vision. These medications may lower pressure by decreasing the amount of fluid produced in the eye, by increasing the amount of fluid exiting through the eye's natural drain, or by providing additional pathways for fluid to leave the eye. Examples of glaucoma drugs include, but are not limited to, betablockers such as, timolol, metipranolol, carteolol, betaxolol, or levobunolol; alpha agonists, such as, brimonidine or iopidine; prostaglandin analogues, such as, latanoprost; carbonic anhydrate inhibitors, such as dorzolamide; cholinergic agonists, such as, pilocarpine or carbachol; and adrenergic agonists, such as, epinephrine or dipivefrin, or combination thereof.

Typically used in treating herpes virus infections of the eye, cytomegalovirus or human Immunodeficiency virus, anti-viral eye medications may be used in conjunction with oral medications for elimination the virus. Examples of anti-virals include, but are not limited to, ganciclovir, acyclovir, valaciclovir, trifluorothymidine, adenine arabinoside or idoxuridine.

The anti-allergy agents decrease the effects of histamine which creates itching, swelling, redness, and watering in the eye. They may work either by preventing the release of histamine in the body or by blocking its effect after it is released. Examples of anti-allergy agents include, but are not limited to, livostin, patanol, cromolyn, alomide or pheniramine.

In some embodiments, the therapeutic agent in the stent is released as an immediate release of the agent or a controlled release of the agent. In some embodiments, the therapeutic agent is coated or attached or embedded in the stent along with one or more of excipients suitable for eye. Such excipients are well known in the art and some of the examples include, but are not limited to, sodium hyaluronate, taurine (or 2-aminoethanesulphonic acid), vitamin E, vitamin A, cytidine-5'-diphosphate choline (CDP-choline), etc.

In another aspect of the present technology, there is provided a stent for treating an eye, composed of a titanium-nickel (Ti—Ni) based shape memory alloy, which stent is self adaptive to a dimension of a vitreous cavity in the eye, wherein the Ti—Ni based shape memory alloy is of an annular shape in a parent phase region and a folded shape in a martensite region, wherein the annular shape has a narrower region with the diameter of about 20 mm and a wider region with the diameter of about 22 mm, and wherein the annular shape has a height of about 5 mm.

Figure 4:
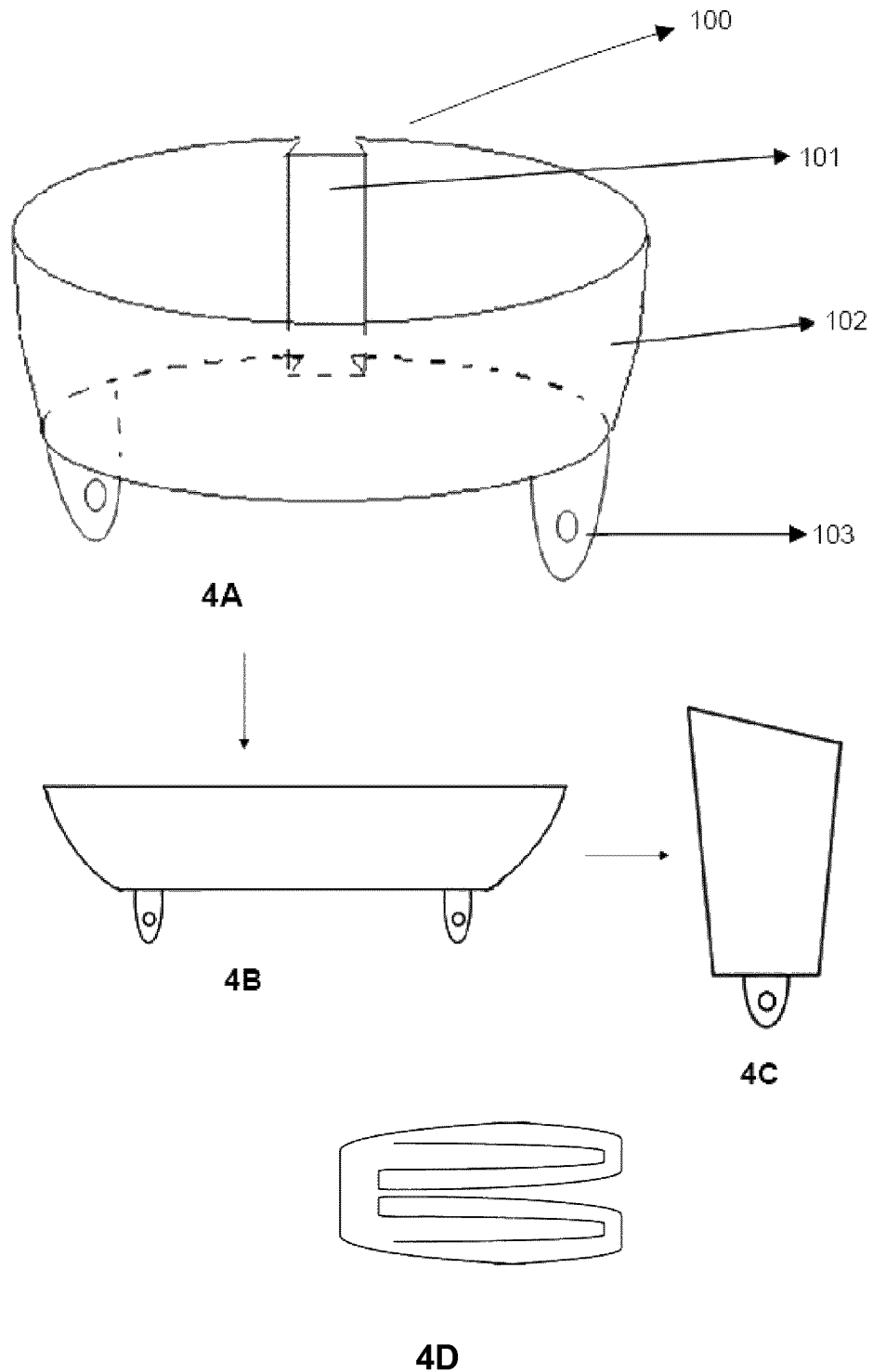
FIG. 4 depicts an illustrative embodiment of the stent of the present technology where the stent is folded into various configurations.
Figure 5:
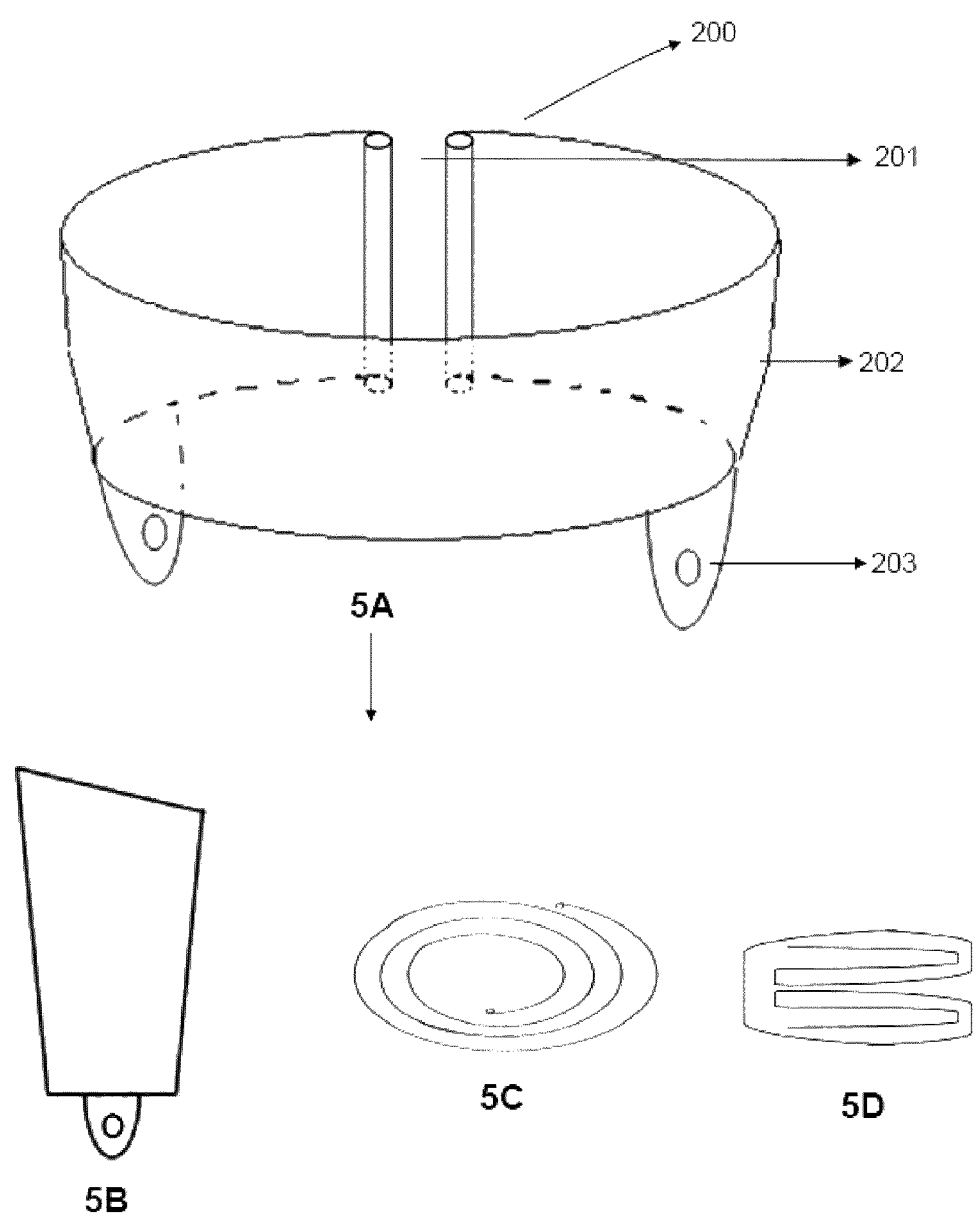
FIG. 5 depicts an illustrative embodiment of the stent of the present technology where the stent is folded into various configurations.

FIGS. 4 and 5 depict illustrative embodiments of the stent of the present technology where the stent is folded into various configurations. It is to be understood that FIGS. 4 and 5 are for illustration purposes only and that other folded configurations of the stent are well within the scope of the present technology. FIG. 4A depicts the annular shape of the stent 100 where the self adaptive zone 101 is a closed region. This stent has been described supra with reference to FIG. 1. Some illustrative embodiments of the folded stent are as shown in FIGS. 4B-D. FIG. 4B is a frontal view of the annular shaped stent 100. FIG. 4C is a frontal view of the stent 100 that is being folded in the middle. FIG. 4D depicts a cross sectional view of the stent 100 that is being folded in the middle.

FIG. 5A depicts the annular shape of the stent 200 where the self adaptive zone 201 is an open region. This stent has been described supra with reference to FIG. 2. Some illustrative embodiments of the folded stent are as shown in FIGS. 5B-D. FIG. 5B is a frontal view of the stent 200 that is being folded in the middle. FIG. 5C is a cross sectional view of the stent that is being rolled or twined inwards. FIG. 5D is a cross sectional view of the stent where each end of the open region of the stent has been folded inwards.

Various methods for making the stent are well known in the art. The stents can be manufactured by methods, such as, but not limited to, laser welding, sputter deposition, wet etching, etc. The manufacturing of the Ti—Ni alloy stents as described in Gupta et al. "Nitinol thin film three-dimensional devices—fabrication and applications," *Proceedings of the International Conference on Shape Memory and Superelastic Technologies* (2004), pages 639-650, is incorporated herein by reference in its entirety.

Methods

In one aspect, the present technology provides a method of treating an ocular disease in a subject, by implanting a stent in an eye of the subject. The stent is composed of a flexible material, and the stent is self adaptive to a dimension of a vitreous cavity in the eye. A "subject" or "patient" of diagnosis or treatment is a mammal, including a human. Non-human animal subjects to diagnosis or treatment include, but are not limited to, murine, such as rats, mice, canine, such as dogs, leporids, such as rabbits, livestock, sport animals, cat, wild animals like tiger or panda, and pets.

The terms "treating," "treatment" and the like refer to obtaining a desired pharmacologic and/or physiologic effect. The effect can be prophylactic in terms of completely or partially preventing a disease or disorder or sign or symptom thereof, and/or can be therapeutic in terms of a partial or complete cure for a disorder and/or adverse effect attributable to the disorder. Examples of "treatment" include, but are not limited to, e.g., preventing a disease from occurring in a subject that may be predisposed or at risk of a disease, such as retinal detachment, but has not yet been diagnosed as having it; inhibiting a disease, i.e., arresting its development; and/or relieving or ameliorating the symptoms of disease or reducing the likelihood of recurrence of the disease, such as retinal detachment or vitreoretinopathy. As is understood by those skilled in the art, "treatment" can include systemic amelioration of the symptoms associated with the pathology and/or a delay in onset of symptoms.

The ocular disease includes any disorder associated with a retinal detachment in the eye. There are various types of retinal detachments, including, but not limited to, rhegmatogenous retinal detachment; exudative, serous, or secondary retinal detachment; and tractional retinal detachment. The rhegmatogenous retinal detachment may occur due to a hole, tear, or break in the retina that may allow fluid to pass from the vitreous space into the subretinal space between the sensory retina and the retinal pigment epithelium. The exudative, serous, or secondary retinal detachment may occur due to inflammation, injury or vascular abnormalities that may result in fluid accumulating underneath the retina without the presence of a hole, tear, or break. The tractional retinal detachment may occur when fibrovascular tissue, caused by an injury, inflammation or neovascularization, pulls the sensory retina from the retinal pigment epithelium.

In some embodiments, other disorders of the eye such as, but are not limited to, inflammation, allergy, virus, infection, glaucoma, neuronal death, anterior ischemic optic neuropathy, neurodegenerative diseases, anoxia and ischemia, peripheral nerve damage, pain, redness, light sensitivity, blurred vision, and the like are treated along with ocular disease as defined above. These other disorders are treated by the therapeutic agent attached or embedded or coated on the stent, as described herein.

The methods of the present technology also include patient population that show symptoms or signs of retinal detachment. Such symptoms include, but are not limited to, e.g., flashing lights, floaters, and a shadow or curtain that affects any part of the vision.

Retinal detachments may be associated with congenital malformations, metabolic disorders, trauma (including previous ocular surgery), glaucoma, vascular disease, choroidal tumors, high myopia or vitreous disease, or degeneration. As noted above, PVR is a disorder that is associated with a retinal detachment in the eye. PVR can occur posteriorly and/or anteriorly with folding of the retina both anteriorly and circumferentially. PVR can be divided into multiple categories based on the configuration of the retina and the location of the scar tissue, and this categorization may be used by eye care specialists to describe the severity and configuration of the retina in PVR.

Figure 6A:
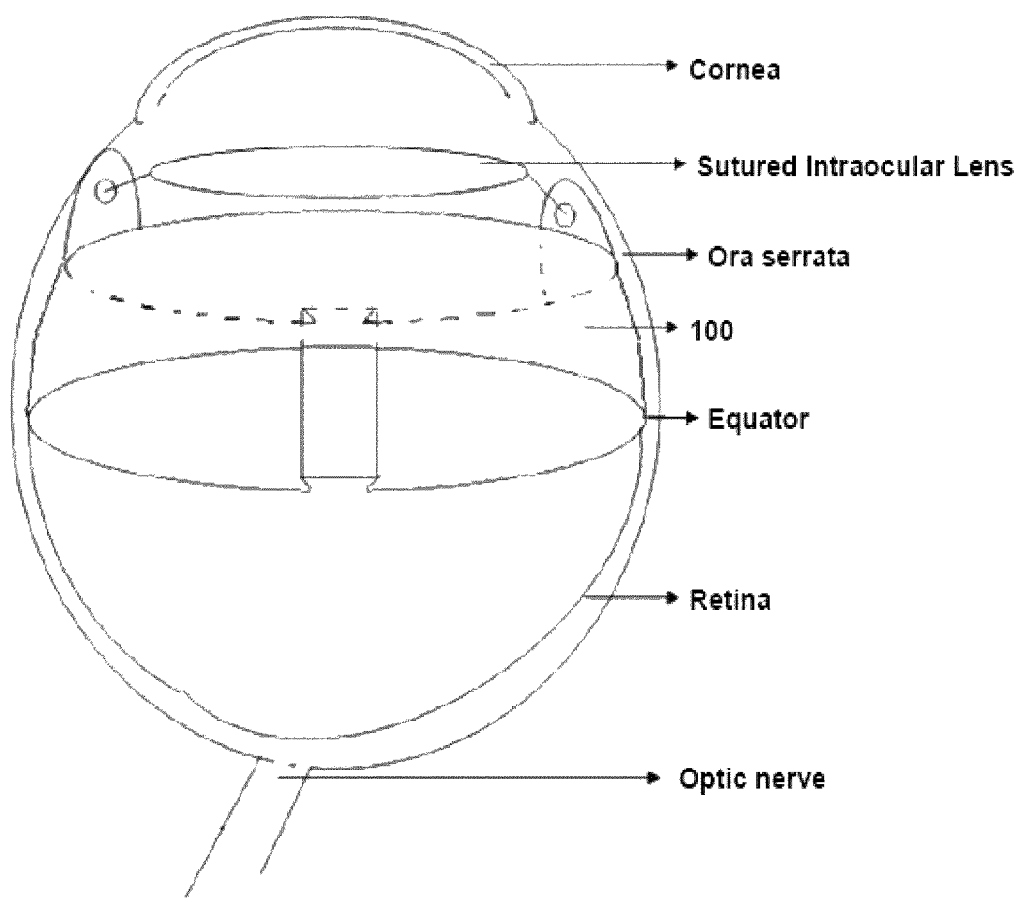
FIG. 6A depicts an illustrative embodiment where the stent with the closed self adaptive zone is depicted as being sutured in the eye.
Figure 6B:
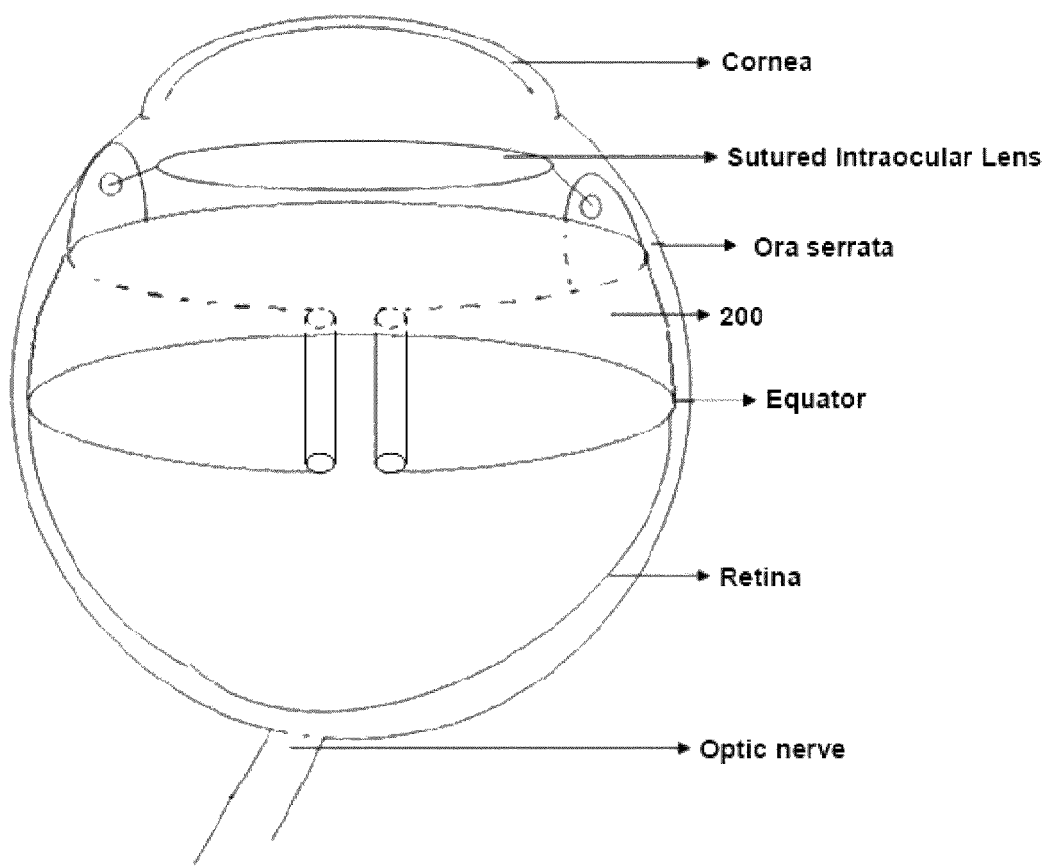
FIG. 6B depicts an illustrative embodiment where the stent with an open self adaptive zone is depicted as being sutured in the eye.

In some embodiments of the present technology, the stent as described above is implanted into the vitreous cavity of the eye. FIGS. 6A and 6B depict illustrative embodiments of the present technology where the stent 100 or 200, respectively, is sutured in the eye. FIG. 6A depicts an illustrative embodiment where the stent 100 with the closed self adaptive zone is depicted as sutured in the eye. FIG. 6B depicts an illustrative embodiment where the stent 200 with an open self adaptive zone is depicted as sutured in the eye. The stent adapts to the dimension of the vitreous cavity of the eye and comes into contact with the detached retina. The stent prevents further detachment of the retina and restores the shape of the retina. In some embodiments, the stent supports a detached retina or proliferative membrane near the equator of the eye. In some embodiments, the stent supports a detached retina or proliferative membrane anterior to an equator of the eye.

In some embodiments, the stent is implanted into a vitreous cavity of the eye by injection. The term "implantation" or "implanting," refers to the delivery of a stent to an appropriate location of the subject or in vitro, where a desired effect is needed. In some embodiments, the stent is injected into the eye using a catheter. In some embodiments, the stent is manually injected into the eye. The injection may comprise an incision on sclera before the injection of the stent into the eye. The stent of the present technology can be folded and injected into vitreous cavity through cornea incision or limbal incision in an aphakic eye or can be injected into vitreous cavity through scleral incision.

In some embodiments of the present technology, the implantation of the stent into the eye further comprises suturing the stent to sclera at the pars plana of ciliary body in the eye.

In one aspect of the present technology, there is provided a method of treating vitreoretinopathy in a subject, by implanting a stent in an eye of the subject wherein the stent is composed of a flexible material, and wherein the stent is self adaptive to a dimension of a vitreous cavity in the eye.

In some embodiments, the implantation of the stent as in the present technology, demonstrates advantages, such as, but not limited to, biocompatibility, reduced number of follow up surgeries, reduced recovery time, reduced time for bed rest, and reduced or no recurrence of retinal detachment.

Kits

In one aspect, the present technology provides a kit comprising a stent for treating an eye, wherein the stent is composed of a flexible material, and wherein the stent is self adaptive to a dimension of a vitreous cavity in the eye.

The kits may further comprise suitable packaging and/or instructions for use of the stent. Kits may also comprise a means for the delivery of the stent, such as syringe, catheter, or other such devices. The kits may further comprise surgical tools.

The kits may also include other compounds for use in conjunction with the stent described herein. Such compounds include, but are not limited to, e.g., alcohol, analgesics, anesthetics, antiseptics, etc. These compounds can be provided in a separate form. The kits may include appropriate instructions for implantation of the stent, side effects, and any other relevant information. The instructions can be in any suitable format, including, but not limited to, e.g., printed matter, videotape, or computer readable disk.

In one embodiment, this technology provides a kit comprising a stent for treating an eye, wherein the stent is composed of a flexible material, and wherein the stent is self adaptive to a dimension of a vitreous cavity in the eye; packaging; and instructions for use.

EXAMPLES

The present technology is further illustrated by the following examples, which should not be construed as limiting in any way.

Example 1

Preparation of a Stent of the Present Technology

A mold for formation of the stent is formed from two coaxial tubes of Teflon® separated by tubular gaskets at each end. The inner tube size is selected according to the desired outer stent diameter, and wall thickness of the gasket is selected according to the desired wall thickness of the stent. Similarly, the dimensions of the mold are selected based on the dimensions of the stent. A desired polymeric mixture is introduced into a transparent mold for formation of the stent. Alternatively, an exemplary polymer can be prepared by mixing a monomers, a cross-linker (Darocur® 1173) and a photoinitiator (hexanediol dimethacrylate) and by placing the mixture into a clear mold. Polymerization is initiated by exposing the mixture to UV light. The polymeric mixture is introduced into the space between the coaxial tubes using a syringe and the mold is then exposed to an ultraviolet light source. Alternatively, the polymeric mixture may be heated if desired. After polymerization, the outer tube is cut away from the mold, the gaskets are removed and the polymer stent is removed from the inner tube.

Example 2

Use of a Stent of the Present Technology

The stent is placed in the eye of a male or a female patient suffering from vitreoretinopathy. The procedure is performed in patients after receiving informed consent from each patient.

All patients undergo stent placement under local anesthetic. The procedure is initiated by performing vitrectomy. Perfluoron or a gas is injected in the eye. The stent of the present technology may already be in a folded state (such as a Ti—Ni alloy stent) or may be folded just before implantation. The stent is manually placed into the vitreous cavity of the eye through a cornea incision or limbal incision in an aphakic eye and a scleral incision in a phakic eye. Alternatively, the stent may be placed into the eye with the help of a catheter. For example, the stent is pushed into the vitreous cavity of the eye with a catheter similar to the folded intraocular lens catheter. After the stent is placed into the eye, it may optionally be sutured to the sclera. An intraocular lens may be sutured to the stent in an aphakic eye. Perfluoron or the gas is replaced with a balanced salt solution.

Follow-up examinations are scheduled for 1 week, 1 month, 3 months, and 6 months after stent placement and at 6-month intervals thereafter. At each visit, eye examination is performed. To assess subjective improvement, the patients are asked to grade their complaints related to vision. All of the patients show improvement in the restoration of the retina in the eye.

EQUIVALENTS

The present disclosure is not to be limited in terms of the particular embodiments described in this application. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A stent for an eye, comprising:
   a flexible material,
   wherein the stent is of an annular shape at a body temperature, and has a distal and a proximal end, and is self-adaptive to a dimension of a vitreous cavity in the eye by a self-adaptive zone which is located at the distal end and has either:
   a single opening which divides the annular shape of the stent along its height; or
   a fold which projects radially inwards and extends along the height of the annular shape of the stent;
   and wherein the self-adaptive zone has a width in a range of about 1-8 mm; and further wherein the stent has a height of about 5 mm.

2. The stent of claim 1, wherein the flexible material is selected from the group consisting of silicon, styrene, polypropylene, polyurethane, poly (caprolactone-β-ethylene oxide), poly (L-lactide-co-glycolide), and polytetrafluoroethylene.

3. The stent of claim 1, wherein the flexible material is an aliphatic ester C1-C50 of acrylic acid or a methacrylic acid ester of polyethyleneoxide.

4. The stent of claim 3, wherein the aliphatic ester C1-C50 of acrylic acid is an aliphatic ester C1-C50 of methacrylic acid.

5. The stent of claim 3, wherein the aliphatic ester C1-C50 of acrylic acid is selected from the group consisting of butyl acrylate, polyarcylic acid, poly(methyl methacrylimide), pentafluoropropylacrylate, polyethylene glycol methacrylate, polyethyleneglycol monomethylether methacrylate, methylmethacrylate, poly(methyl methacrylate), isobornyl methacrylate, isobutyl methacrylate, perfluoroacetylmethacrylate, tertiary butylmethacrylate, phenylethylmethacrylate, hydroxyethyl methacrylate, glycerol methacrylate, and heptadecylfluorodecyl-methacrylate.

6. The stent of claim 3, wherein the methacrylic acid ester of polyethyleneoxide is polyethyleneglycol dimethacrylate, polyethyleneglycol methacrylate or polyethyleneglycol acrylate.

7. The stent of claim 1, wherein the flexible material is a shape memory substance.

8. The stent of claim 7, wherein the shape memory substance is a titanium-nickel (Ti—Ni) based shape memory alloy or polymer thereof.

9. The stent of claim 8, wherein the Ti—Ni based shape memory alloy comprises Ti at about 43.5 wt % to about 52 wt % and Ni at about 48 wt % to about 56.5 wt %.

10. The stent of claim 8, wherein the Ti—Ni based shape memory alloy is of an annular shape at a body temperature and a folded shape at room temperature.

11. The stent of claim 1, wherein the flexible material is a biodegradable material.

12. The stent of claim 11, wherein the biodegradable material is poly (caprolactone-β-ethylene oxide) or poly (L-lactide-co-glycolide).

13. The stent of claim 1, wherein the annular shape has a diameter which approximates a diameter of the vitreous cavity of the eye.

14. The stent of claim 1, further comprising one or more projections for fixing the stent in the eye.

15. The stent of claim 1, further comprising a therapeutic agent.

16. A method of treating an ocular disease in a subject, comprising:
    implanting a stent in an eye of the subject wherein the stent comprises a flexible material,
    wherein the stent is of an annular shape at a body temperature, and has a distal and a proximal end, and is self-adaptive to a dimension of a vitreous cavity in the eye by a self-adaptive zone which is located at the distal end and has either:
        a single opening which divides the annular shape of the stent along its height; or
        a fold which projects radially inwards and extends along the height of the annular shape of the stent;
    and wherein the self-adaptive zone has a width in a range of about 1-8 mm; and further wherein the stent has a height of about 5 mm.

17. The method of claim 16, wherein the ocular disease is vitreoretinopathy.

18. The stent of claim 1, wherein the flexible material is a non-biodegradable material.

19. The stent of claim 18, wherein the non-biodegradable material is a Ti—Ni based shape memory alloy, poly(acrylic acid), and poly(methyl methacrylimide).

* * * * *